United States Patent
Koh et al.

(10) Patent No.: US 9,304,128 B1
(45) Date of Patent: Apr. 5, 2016

(54) TOXIN ACTIVITY ASSAYS, DEVICES, METHODS AND SYSTEMS THEREFOR

(71) Applicant: Sandia Corporation, Albuquerque, NM (US)

(72) Inventors: Chung-Yan Koh, Dublin, CA (US); Ulrich Y. Schaff, Livermore, CA (US); Gregory Jon Sommer, Livermore, CA (US)

(73) Assignee: Sandia Corporation, Albuquerque, NM (US)

( * ) Notice: Subject to any disclaimer, the term of this patent is extended or adjusted under 35 U.S.C. 154(b) by 72 days.

(21) Appl. No.: 14/157,278

(22) Filed: Jan. 16, 2014

Related U.S. Application Data

(60) Provisional application No. 61/759,486, filed on Feb. 1, 2013.

(51) Int. Cl.
*G01N 33/53* (2006.01)
*C12Q 1/68* (2006.01)
*G01N 33/543* (2006.01)

(52) U.S. Cl.
CPC ................................ *G01N 33/54306* (2013.01)

(58) Field of Classification Search
None
See application file for complete search history.

(56) References Cited

U.S. PATENT DOCUMENTS

| | | | |
|---|---|---|---|
| 3,555,284 A | 1/1971 | Anderson | |
| 3,744,974 A | 7/1973 | Maddox et al. | |
| 4,125,375 A | 11/1978 | Hunter | |
| 4,156,570 A | 5/1979 | Wardlaw | |
| 4,656,143 A | 4/1987 | Baker et al. | |
| 4,683,579 A | 7/1987 | Wardlaw | |
| 4,844,818 A | 7/1989 | Smith | |
| 5,279,936 A | 1/1994 | Vorpahl | |
| 5,635,362 A | 6/1997 | Levine et al. | |
| 5,705,628 A | 1/1998 | Hawkins | |
| 5,882,903 A | 3/1999 | Andrevski et al. | |
| 6,153,148 A | 11/2000 | Thomas | |
| 6,319,469 B1 | 11/2001 | Mian et al. | |
| 6,503,722 B1 * | 1/2003 | Valkirs | 435/7.2 |
| 6,887,384 B1 | 5/2005 | Frechet et al. | |
| 7,033,747 B2 | 4/2006 | Gordon et al. | |
| 7,157,049 B2 | 1/2007 | Valencia et al. | |
| 7,758,810 B2 | 7/2010 | Lee et al. | |
| 2001/0055812 A1 | 12/2001 | Mian et al. | |
| 2002/0098535 A1 | 7/2002 | Wang et al. | |
| 2002/0137068 A1 | 9/2002 | Haugland et al. | |
| 2002/0151043 A1 | 10/2002 | Gordon | |
| 2002/0164659 A1 | 11/2002 | Rao et al. | |
| 2003/0124719 A1 | 7/2003 | Woodside | |
| 2004/0072278 A1 | 4/2004 | Chou et al. | |
| 2005/0215410 A1 | 9/2005 | Merino et al. | |
| 2005/0282220 A1 | 12/2005 | Prober et al. | |
| 2009/0004059 A1 | 1/2009 | Pugia et al. | |
| 2009/0069554 A1 | 3/2009 | Finne | |
| 2009/0209402 A1 | 8/2009 | Andersson | |
| 2009/0325186 A1 | 12/2009 | Hinnah et al. | |
| 2010/0068754 A1 | 3/2010 | Kirakossian | |
| 2010/0120596 A1 | 5/2010 | Froman et al. | |
| 2010/0151560 A1 | 6/2010 | Wo et al. | |

FOREIGN PATENT DOCUMENTS

| WO | WO-2008/143578 | 11/2008 |
|---|---|---|
| WO | WO-2009/098237 | 8/2009 |

OTHER PUBLICATIONS

Abi-Samra, Kameel et al., "Infrared controlled waxes for liquid handling and storage on a CD-microfluidic platform", The Royal Society of Chemistry; Lab on a Chip, 2011, 723-726.

Ahanotu, et al., "Staphylococcal Enterotoxin B as a Biological Weapon: Recognition, Management, and Surveillance of Staphylococcal Enterotoxin", Applied Biosafety; vol. 11 (3), 2006, 120-126.

Albrecht, J.W. et al., "Micro Free-Flow IEF Enhanced Active Cooling and Functionalized Gels", Electrophoresis, 2006, pp. 4960-4969, vol. 27.

Amersham, , "Percoll: Methodology and Applications", 2001, 1-84.

Amukele, et al., "Ricin A-chain activity on stem-loop and unstructured DNA substrates.", Biochemistry; vol. 44(11), Mar. 25, 2005, 4416-4425.

Andersson, et al., "Parallel nanoliter microfluidic analysis system", Analytical Chem. 79, 4022 (2007).

Baldwin, Robert L. , "How Hofmeister Ion Interactions Affect Protein Stability", Biophysical Journal; vol. 71, Oct. 1996, 2056-2063.

Berry, Scott M., "One-step Purification of Nucleic Acid for Gene Expression Analysis via Immiscible Filtration Assisted by Surface Tension", Lap Chip, May 21, 2011, 11 (10): 1747.

(Continued)

*Primary Examiner* — James Martinell
(74) *Attorney, Agent, or Firm* — Dorsey & Whitney, LLP

(57) ABSTRACT

Embodiments of the present invention are directed toward devices, system and method for conducting toxin activity assay using sedimentation. The toxin activity assay may include generating complexes which bind to a plurality of beads in a fluid sample. The complexes may include a target toxin and a labeling agent, or may be generated due to presence of active target toxin and/or labeling agent designed to be incorporated into complexes responsive to the presence of target active toxin. The plurality of beads including the complexes may be transported through a density media, wherein the density media has a lower density than a density of the beads and higher than a density of the fluid sample, and wherein the transporting occurs, at least in part, by sedimentation. Signal may be detected from the labeling agents of the complexes.

25 Claims, 13 Drawing Sheets

(56) References Cited

OTHER PUBLICATIONS

Boyko, Matthew et al., "Cell-Free DNA—a Marker to Predict Ischemic Brain Damage in a Rat Stroke Experimental Model", Journal of Neurosurg Anesthesiol, vol. 23, No. 3, Jul. 2011, 222-228.
Brigotti, et al., "Shiga toxin 1 acting on DNA in vitro is a heat-stable enzyme not requiring proteolytic activation", Biochimie Journal; 86(45), 2004, 305-309.
Carney, J., "Rapid Diagnostic Tests Employing Latex Particles", Analytical Proceedings, Apr. 1990, 99-100, vol. 27.
Curtis, R. A. et al., "A Molecular approach to bioseparations: Protein-protein and protein-salt interactions", Chemical Engineering Science; vol. 61, 2006, 907-923.
Czeiger, David et al., "Measurement of Circulating Cell-Free DNA Levels by a New Simple Fluorescent Test in Patients With Primary Colorectal Cancer", Am J Clin Pathol, 2011, 264-270.
Endo, et al., "RNA N-Glycosidase Activity of Ricin A-chain. Mechanism of Action of The Toxic Lectin Ricin on Eukaryotic Ribosomes", The Journal of Biological Chemistry, vol. 262, No. 17, Jun. 15, 1987, 8128-8130.
Glorikian, Harry et al., "Smart-consumables product development: Implications for molecular diagnostics", DX Direction, 2010, 12-16.
Goldshtein, Hagit et al., "A Rapid Direct Fluorescent Assay for Cell-Free DNA Quantification in Biological Fluids", Annals of Clinical Biochemistry, 2009, 488-494.
Gorkin, et al., "Centrifugal microfluidics for biomedical applications", www.rsc.org/loc; Lab on a Chip, May 2010, 1758-1773.
Holmberg, et al., "Depurination of A4256 in 28 S rRNA by the Ribosome-inactivating Proteins from Barley and Ricin Results in Different Ribosome Conformations", Journal of Molecular Biology; vol. 259(1), May 31, 1996, 81-94.
Holmes, David et al., "Leukocyte analysis and differentiation using high speed microfluidic single cell impedance cytometry", Lab on a Chip 9, Aug. 7, 2009, 2881-2889.
Huang, et al., "The Primary Structure of Staphylococcal Enterotoxin B. III. The Cyanogen Bromide Peptides of Reduced and Aminoethylated Enterotoxin B, and The Complete Amino Acid Sequence.", The Journal of Biological Chemistry vol. 245 No. 14, Jul. 25, 1970, 3518-3525.
International Search Report and Written Opinion dated Jun. 28, 2013 for PCT/US2013/032349.
Lee, et al., "Fully integrated lab-on-a-disc for simultaneous analysis of biochemistry and immunoassay from whole blood", Lab Chip, 2011, 11: 70-78.
Lee, B. S. et al., "A fully automated immunoassay from whole blood on a disc", Lab on a Chip 9, Mar. 5, 2009, 1548-1555.
Lim, C. T. et al., "Bead-based microfluidic immunoassays: The next generation", Biosensors Bioelectronics 22, Jul. 20, 2006, 1197-1204.
Lo, C.T. et al., "Photopolymerized Diffusion-Defined Polyacrylamide Gradient Gels for On-Chip Protein Sizing", The Royal Society of Chemistry, Lab on a Chip, vol. 8, No. 8, 2008, pp. 1273-1279.
Lo, Y. M. D. et al., "Plasma DNA as a Prognostic Marker in Trauma Patients", Clinical Chemistry 46:3, 2000, 319-323.
Madou, Marc et al., "LAB on a CD", Annual Rev. Biomed Eng 8, May 2006, 601-628.
Maes, Melissa L. et al., "Comparison of Sample Fixation and the use of LDS-751 or anti-CD45 or Leukocyte Identification in Mouse Whole Blood for Flow Cytometry", Journal of Immunological Methods, 319(1-2) Jan. 30, 2007, 79-86.
Min, Junhong et al., "Functional Integration of DNA Purification and Concentration Into a Real Time Micro-PCR Chip", The Royal Society of Chemistry; Lab on a Chip, 2011, 259-265.
Price, Christopher P. et al., "Light-Scattering Immunoassay", Principles and Practice of Immunoassay (Second Edition); Chapter 18, 1997, 445-480.
Rhodes, Andrew et al., "Plasma DNA concentration as a predictor of mortality and sepsis in critically ill patients", Critical Care, 2006, 1-7.
Rider, Todd H. et al., "A B Cell-Based Sensor for Rapid Identification of Pathogens", www.sciencemag.org; Science vol. 301, Jul. 11, 2003, 213-215.
Riegger, L. et al., "Read-out concepts for multiplexed bead-based fluorescence immunoassays on centrifugal microfluidic platforms", Sensors and Actuators A—Physical, 2006, 455-462.
Saukkonen, et al., "Cell-Free Plasma DNA as a Predictor of Outcome in Severe Sepsis and Septic Shock", Clinical Chemistry; vol. 54:6, 2008, 1000-1007.
Schaff, et al., "Whole Blood Immunoassay Based on Centrifugal Bead Sedimentation", Clinical Chemistry Automation and Analytical Techniques 57:5, 2011, 753-761.
Schembri, et al., "Portable Simultaneous Multiple Analyte Whole-Blood Analyzer for Point-of-Care Testing", Clinical Chemistry 38/9, 1992, 1665-1670.
Schneider, et al., "Characterization of EBV-Genome Negative "Null" and "T" Cell Lines Derived From Children With Acute Lymphoblastic Leukemia and Leukemic Transformed Non-Hodgkin Lymphoma", International Journal of Cancer; 19(5), May 15, 1977, 621-626.
Yu, et al., "Bioinformatic processing to identify single nucleotide polymorphism that potentially affect Ape1 function.", Mutation Research/Genetic Toxicology and Environmental Mutagenesis; vol. 722(2), Jun. 17, 2011, 140-146.
Zhang, L. et al., "A New Biodosimetric Method: Branched DNA-Based Quantitative Detection of B1 DNA in Mouse Plasma", The British Journal of Radiology, vol. 83, Aug. 2010, 694-701.
Ziegler, Annemarie et al., "Circulating DNA: a new diagnostic gold mine?", Cancer Treatment Reviews, vol. 28, 2002, 255-271.
McBain et al., Polyethyleneimine functionalized iron oxide nanoparticles as agents for DNA delivery and transfection, Journal of Materials Chemistry, 17, pp. 2561-2565, available online Apr. 13, 2007.
Riahi et al. Analytical Chemistry. 2011. 83(16): 6349-6354 and Supporting Information.
Melting Temperature Calculation. Retrieved on asf from the internet: http://www.biophp.org/minitools/melting_temperature/demo.php?primer=CGT+TAC+CCG+CAG&basic-1&NearestNeighbor=1&cp=200&cs=50&cmg=0, Accessed Jul. 30, 2015.
Berlier et al. The Journal of Histochemistry and Cytochemistry. 2003. 51(12): 1699-1712.

\* cited by examiner

101 — ADDING MODIFIED BEADS TO A FLUID SAMPLE WITH ACTIVE TOXIN, THE ACTIVE TOXIN ATTACKING A DNA/RNA LOOP LINKED TO THE MODIFIED BEAD CAUSING DEPURINATION OF THE DNA/RNA LOOP, GENERATING COMPLEXES ON BEADS IN A FLUID SAMPLE, THE COMPLEXES INCLUDING A TARGET ANALYTE AND LABELING AGENT

102 — ADDING LABELING AGENT, ATTACHING LABELING AGENT TO DEPURINATED DNA/RNA LOOP TO FORM A COMPLEX

103 — TRANSPORTING THE BEADS THROUGH A DENSITY MEDIA HAVING A DENSITY LOWER THAN THE BEADS AND HIGHER THAN THE FLUID SAMPLE

104 — DETECTING SIGNAL FROM THE LABELING AGENT OF THE COMPLEXES

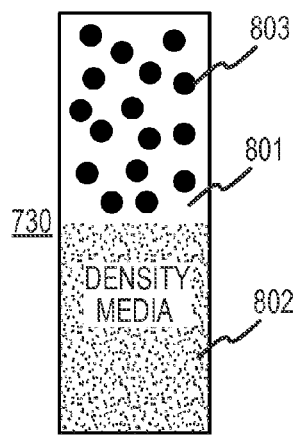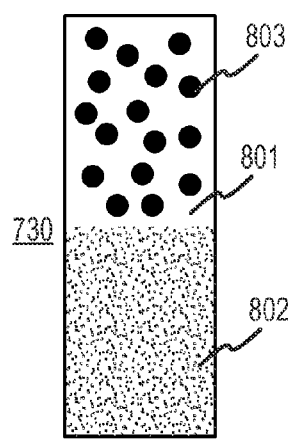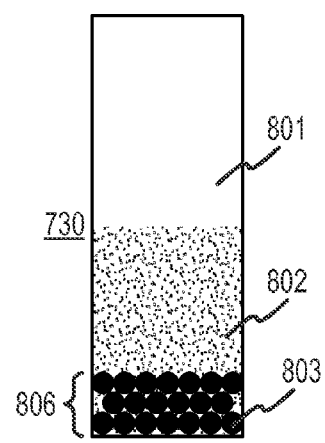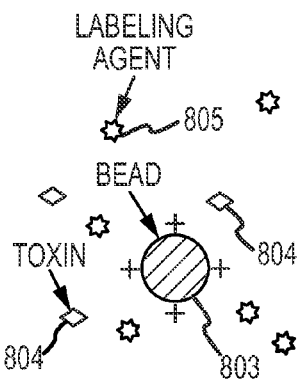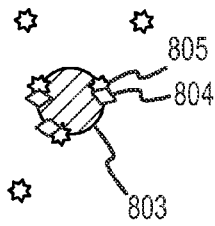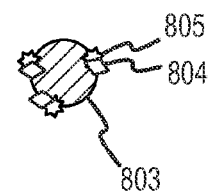
FIG.8　　　FIG.9　　　FIG.10

TOXIN ACTIVITY ASSAYS, DEVICES, METHODS AND SYSTEMS THEREFOR

CROSS-REFERENCE TO RELATED APPLICATION

This application claims benefit under 35 U.S.C. 119(e) to U.S. provisional patent application Ser. No. 61/759,486, entitled "METHOD FOR DETECTION OF TOXIN ACTIVITY IN MICROFLIUDIC DISKS" filed Feb. 1, 2013, which provisional application is incorporated herein by reference in its entirety for any purpose.

STATEMENT REGARDING RESEARCH & DEVELOPMENT

This invention was developed under Contract DE-AC04-94AL85000 between Sandia Corporation and the U.S. Department of Energy. The U.S. Government has certain rights in the invention.

TECHNICAL FIELD

Embodiments of the invention relate generally to assay systems and examples include methods, systems, and apparatus for conducting assays, including the detection and/or quantification of active toxin such as but not limited to Ricin toxin, Shiga-like toxins (SLT), and Staphylococcal Enterotoxin B (SEB).

BACKGROUND

Ricin, Shiga-like toxins (SLT) and Staphylococcal enterotoxin B (SEB) have either been used as bioterrorism agents or are considered a bioterrorism threat because of their extreme toxicity and ease of administration. These toxins can be easily administered by inhalation, injection or ingestion. In the event of a mass exposure to biological toxins, identification of the agent in question is important for accurate diagnostic assessment of affected patients. It may also, however, be important to determine the fraction of the toxin which is still active; for example, if a significant fraction of the toxin is inactive, a treatment may not be as aggressive as it would be when a large fraction of the toxin is active. Distinguishing between active and inactive toxin may be advantageous because of the possibility that genetically engineered toxins, including the enzymatic portion of the toxin and a binding domain of another protein, can be used as a bioweapon agent, and may not be captured by traditional qualitative toxin detection tests.

Ricin is a highly toxic protein produced by *Ricinus communis* or castor bean plant. It is a category B agent, under the Biological Select Agents or Toxins, as defined by the United States Department of Human and Health Services. The major symptoms of ricin poisoning depend on the route of exposure and the dose received, though many organs may be affected in severe cases. The likely symptoms of Ricin inhalation include respiratory distress (difficulty breathing), fever, cough, nausea, and tightness in the chest. Finally, low blood pressure and respiratory failure may occur, leading to death. Swallowing of Ricin would likely lead to vomiting and diarrhea. Severe dehydration may also result. Other signs or symptoms may include seizures, and blood in the urine. Within several days, the person's liver, spleen, and kidneys might stop working, and the person could die. Ricin is unlikely to be absorbed through normal skin. Death from ricin poisoning could take place within 36 to 72 hours of exposure, depending on the route of exposure (inhalation, ingestion, or injection) and the dose received.

Shiga-like toxins (SLTs) are a class of toxins produced by pathogenic *Escherichia coli* strains. They cause hemolytic uremic syndrome in humans, which may lead to death.

Currently, there are no portable quantitative activity assays available for determining activity of Ricin and Shiga-like toxins. The mechanism of action of these toxins generally does not cause a break in nucleic acid phosphodiester backbone, making it difficult to determine activity. Accordingly, available assays are qualitative in nature, only determining presence or absence of these toxins in a sample, without giving any information regarding their activity. Further, the few quantitative assays that are available include tedious processes and steps. For instance, cell-free translation assays for determining activity of Ricin toxin require cell-extracts that provide transcriptional and translational molecular machinery including RNA polymerases for mRNA transcription, ribosomes for polypeptide translation, tRNA and amino acids, enzymatic cofactors and energy source, and cellular components essential for protein folding, while cytotoxicity assays for determining biological activity require bacterial or tissue culture cell. Alternatively, mass-spectrometry may be used for detecting free adenine released in a sample after Ricin attack on ribosomes, or HPLC-ESI-MS is used for detecting Ricinine, a marker of Ricin. The processes involving mass-spectrometry suffer from background noise and reduced sensitivity due to presence of interfering components in a sample; not to mention cumbersome equipment that is not portable.

Not only are these processes labor-intensive, they are also time-intensive. For instance, the rapid detection tests used by Center for Disease Control and Prevention's Laboratory Response Network take 6-8 hours, while the toxin activity tests take about 48 hours. Although there have been reports of new detection assays that only take 1-2 hours, these assays are only qualitative in nature and do not give any information on activity of the toxin. Staphylococcal enterotoxin B (SEB) is an enterotoxin produced by the bacterium *Staphylococcus aureus*. It is a common cause of food poisoning, with severe diarrhea, nausea and intestinal cramping often starting within a few hours of ingestion. SEB is classified as an incapacitating agent because in most cases aerosol exposure does not result in death but in a temporary, though profoundly incapacitating, illness lasting as long as 2 weeks. SEB is a superantigen, which causes massive nonspecific activation of immune system causing release of large amounts of cytokines that lead to significant inflammation.

Currently, there are no assays available for determining activity of SEB. The assays available, such as enzyme-linked immunosorbent assays (ELISA), chemiluminescence (ECL), and polymerase chain reaction (PCR), are quantitative in nature and only aid in detection of SEB.

Microfluidic systems, including "lab on a chip" or "lab on a disk" systems continue to be in development. See, Lee, B. S., et. al., "A fully automated immunoassay from whole blood on a disc," Lab Chip 9, 1548-1555 (2009) and Madou, M. et. al., "Lab on a CD," Annu. Rev. Biomed. Engr. 8, 601-628 (2006), which articles are hereby incorporated by reference in their entirety for any purpose.

BRIEF DESCRIPTION OF THE DRAWINGS

FIG. 1 is a flowchart illustrating method for conducting a Ricin/SLT activity assay in accordance with embodiments of the present invention.

Figure 2A:
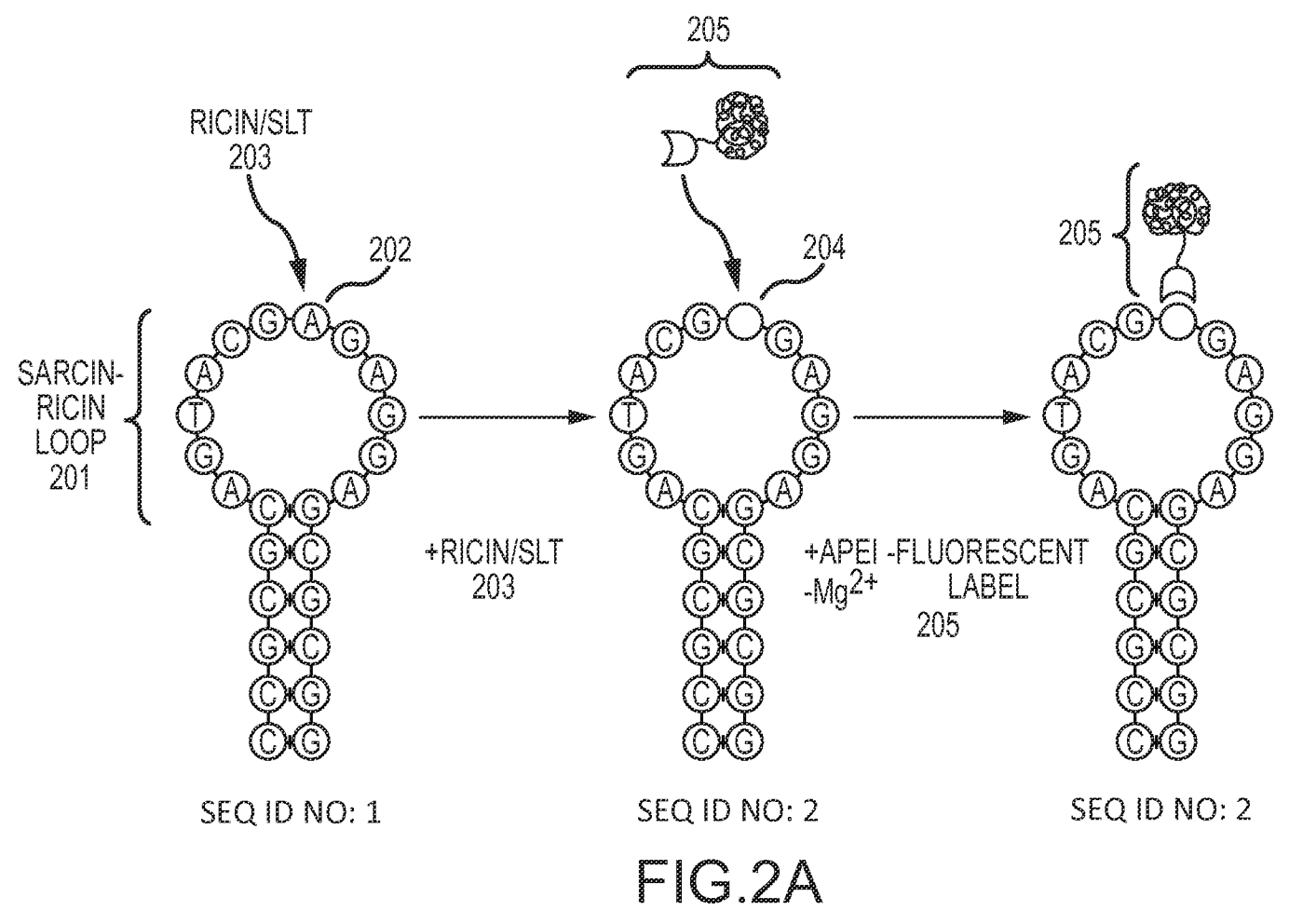

FIGS. 2A and 2B are schematic illustrations of a Ricin/SLT activity assay in accordance with embodiments of the present invention.

FIGS. 8-10 are schematic illustrations of a detection region containing a sample fluid and a density media in accordance with an embodiment of the present invention.

Figures 12, 13:
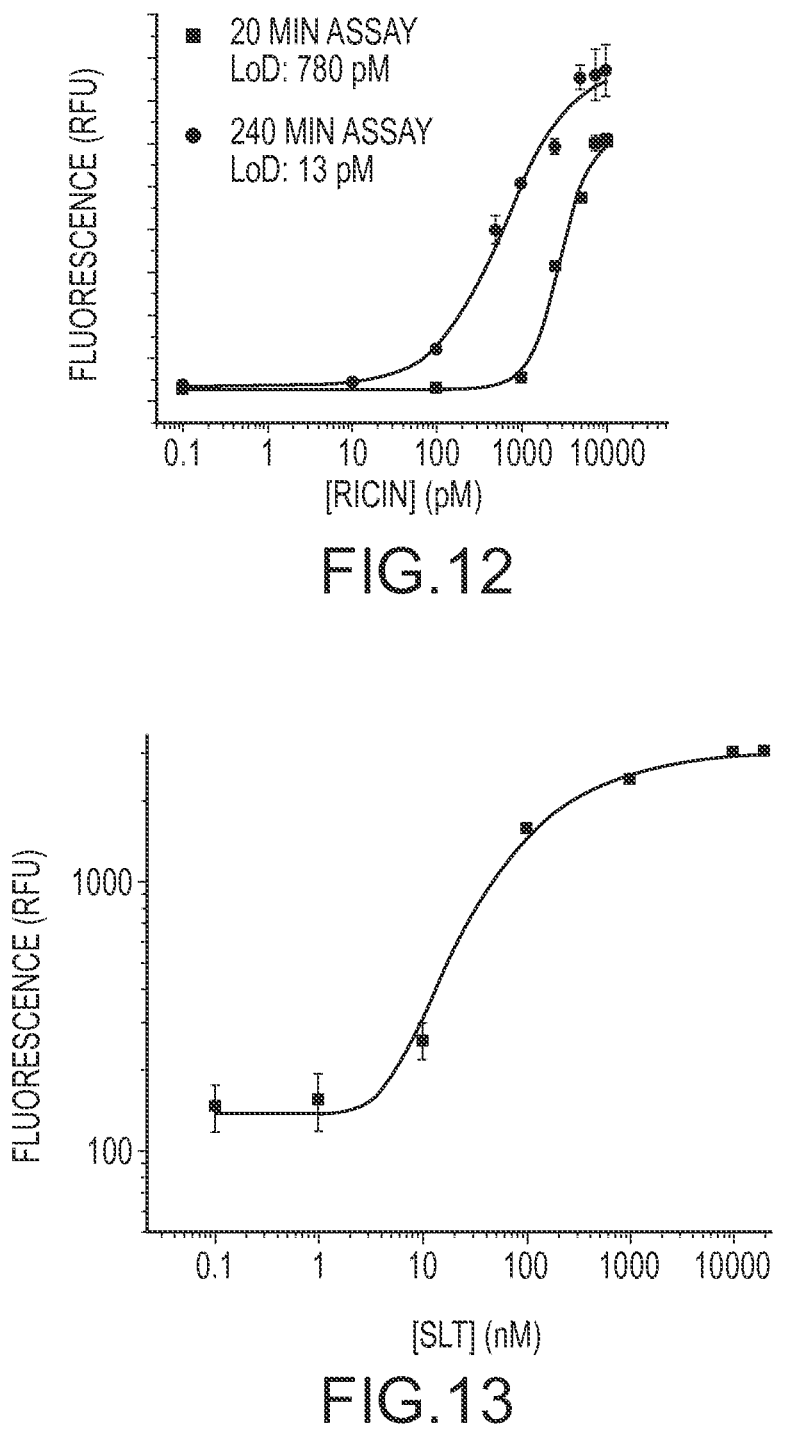

FIG. 12 shows a dose response curve generated using serial dilutions of Ricin in accordance with embodiments of the present invention.

FIG. 13 shows a dose response curve generated using serial dilutions of SLT in accordance with embodiments of the present invention.

DETAILED DESCRIPTION OF PREFERRED EMBODIMENTS

Figure 2B:
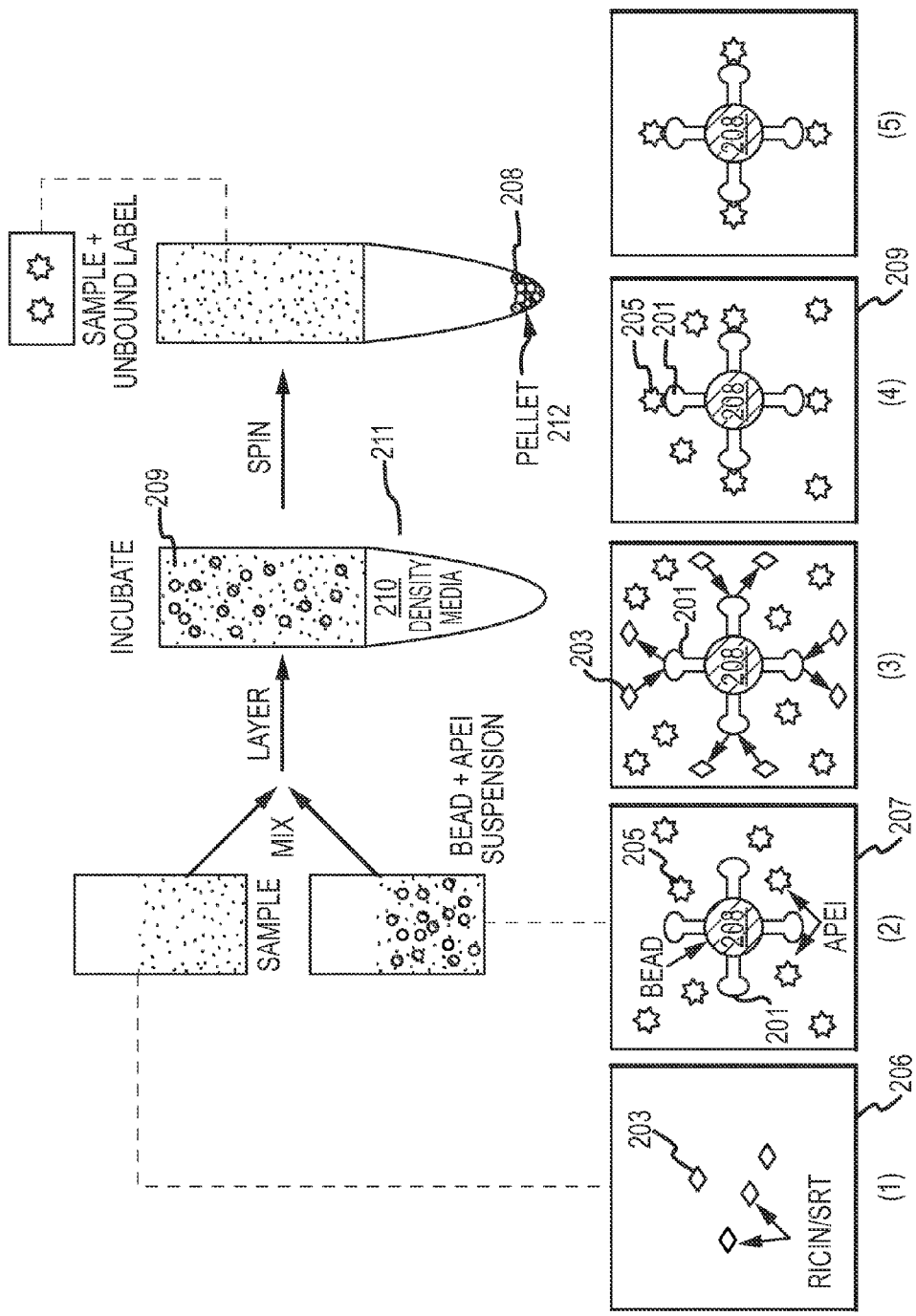

Certain details are set forth below to provide a sufficient understanding of embodiments of the invention. However, it will be clear to one skilled in the art that embodiments of the invention may be practiced without various of these particular details. In some instances, well-known chemical structures, chemical components, molecules, materials, microfluidic components, electronic components, electronic circuits, control signals, timing protocols, and software operations have not been shown in detail in order to avoid unnecessarily obscuring the described embodiments of the invention.

Embodiments of the present invention include systems, apparatuses, and methods for detecting and/or quantifying Ricin, SLTs and SEB toxin in a sample. As mentioned above, existing methods for detecting these toxins are generally either limited to only qualitative detection, and not activity determination, or are cumbersome and time-intensive. Examples according to the current invention include analysis of target analytes including toxins such as but not limited to Ricin, SLTs or SEB. References will be made herein to and examples given of applications targeting Ricin, SLTs or SEB, but it should be understood that in other examples, other toxins may also be targeted for detection and/or quantification. In examples according to the present invention, the presence of active toxin may be detected and/or quantified. Active toxin generally refers to toxin that is able to act on its designated target or targets. Active toxin generally does not include toxin which may be present but, for whatever reason, is unable to act (e.g. cleave or bind) on its designated target or targets.

Assays described herein may be conducted using systems and devices that utilize sedimentation to perform assays. For example, co-pending U.S. application Ser. No. 12/891,977, filed Sep. 28, 2010, entitled "Devices, systems, and methods for conducting sandwich assays using sedimentation," is hereby incorporated by reference in its entirety for any purpose. The aforementioned application includes examples of the formation of complexes including a capture agent, target analyte, and labeling agent on sedimentation particles. Thus, target analytes may be separated from sample by affinity with a capture agent, and the sedimentation particles passed through a density medium to pellet out at a detection region of a microfluidic disk. Examples of systems and devices described in the aforementioned application may be utilized to conduct assays described herein.

Examples of the present invention include methods, systems, and devices, for performing assays to detect ricin, shiga-like toxins, or both. Ricin generally acts by inhibiting protein synthesis. It is approximately 64 kDa in size and is composed of two chains joined by a single disulfide bond. The A chain is generally responsible for Ricin's catalytic enzymatic activity, while the B chain is generally responsible for binding to cell surface receptors on the cell membrane and facilitating entry of the toxin in to the cytosol. Ricin generally inhibits protein synthesis by inactivating ribosomes by attacking the sarcin-ricin loop. This loop is a highly conserved sequence of nucleotides generally found in the 28S RNA of the large subunit of ribosomes. It has a conformation of a loop and is generally cleaved by both α-sarcin and ricin. Ricin generally acts by specifically and irreversibly hydrolyzing the N-glycosidic bond of the single adenine residue at position 4324 (A4324) in the sarcin-ricin loop within the 28S rRNA, releasing the base, but leaving the phosphodiester backbone of the RNA intact. Inactive ricin may be unable to perform this action. The process of attacking and releasing A4324 is generally referred to as depurination. The sarcin-ricin loop may be important in binding elongation factors during protein synthesis; however, depurination by Ricin may prevent this binding causing inactivation of ribosome, resulting in toxicity by inhibition of protein synthesis.

Shiga-like toxins have a similar mechanism of action as Ricin; they also generally act by depurinating A4324 and thereby inhibiting protein synthesis. Since both ricin and shiga-like toxins act by similar mechanisms, generally the same activity assays may be utilized for both Ricin and SLTs. Further, there may be other toxins that also act by attacking highly conserved sequences of different conformations. The same activity assays may also be utilized for such toxins.

In an example of an activity assay suitable for detection of active ricin, SLTs or combinations thereof, depurination caused by the toxins may be used to determine their activity. Generally, a labeled enzyme may be used to bind to a site created by an active toxin attack. For example, a fluorescently-labeled human Apurinic/apyrimidinic (AP) endonuclease (APE1) enzyme may be used to bind to the abasic site (i.e., a site without a base, for example, without A4324) left after an attack by the toxins to detect depurination, hence the activity of the toxin. The enzyme may generally be labeled with quantum dots (e.g. QDot 585 from Molecular Probes), alexa fluor 647 or 10 nm latex particles loaded with dye. Typically, APE1 participates in the DNA base excision repair (BER) pathway by nicking the phosphodiester backbone at an AP site (a site without a base, for example, without A4324) through acyl substitution after a DNA glycosylase removes a damaged or inappropriate base. This process is mediated by $Mg^{2+}$ ions, which stabilize the AP site and cause release of APE1 from the site to allow for other enzymes to continue with the BER pathway. In ricin, SLT, or both, activity assays, binding of fluorescently labeled APE1 is desired while preventing enzyme turnover. This is achieved, for example, by depriving APE1 of $Mg^{2+}$ ions. Thus, APE1 binds to the damaged DNA substrate without acting to complete the repair, leading to detection of depurination caused by Ricin/SLTs activity. Another advantage of using APE1 in detection assays is its higher affinity for an abasic site. Unlike other enzymes that may recognize an abasic site, APE1 is involved in the BER pathway, which makes it a very strong candidate for detection of depurination.

FIG. 1 is a flowchart illustrating a method for conducting an activity assay for ricin, SLTs, or combinations thereof, in accordance with embodiments of the present invention. In block 101, an active toxin attacks a loop linked to a bead causing depurination of the DNA substrate, giving rise to an abasic site. In block 102, a labeling agent attaches to the abasic site, forming a complex. The complexes may be generated on sedimentation particles (e.g., beads) in a fluid sample. The complexes may include the loop targeted by the toxin and the labeling agent. Block 102 may be followed by block 103. In block 103, the sedimentation particles, e.g., the complexes, may be transported through a density media having a lower density than the beads but higher than the fluid sample. Gravitational forces generated naturally or by centrifugation may be used to transport the beads through the density media. The sedimentation particles accordingly may sediment out of the fluid sample, forming a concentrated pellet at a peripheral portion of a chamber. Block 103 may be followed by block 104. In block 104, a signal may be detected from the labeling agent of the complexes. In some examples, by separating the sedimentation particles from the sample fluid using gravitational forces, the beads are also concentrated, which may eliminate or reduce a need for amplification of the labeling agent.

In block 103, complexes including the target analyte (e.g., a toxin), and labeling agent may be formed on beads in a fluid sample. Any sedimentation particles with appropriate surface properties, including beads, may be used, including but not limited to, polystyrene beads, silica beads or poly(methyl methacrylate) (PMMA) beads. Substantially any bead radii may be used. Examples of beads may include beads having a radius from 150 nanometers to 10 microns.

In Ricin/SLTs activity assays described herein, the beads used to implement the method described with reference to FIG. 1 may have surface modifications to enable attack by ricin, SLT, or combinations thereof. For example, synthetic DNA stem loop substrate, e.g., the sarcin-ricin loop, may be covalently linked to silica beads. A DNA substrate may be chosen instead of an RNA substrate due, for example, to ability of the toxins to act on DNA, as well as due, for example, to a greater stability of DNA compared to RNA. Similarly, the labeling agent may be any suitable agent for binding to the target abasic site (AP site) and providing a detection signal. For example, aforementioned APE1 may have a high affinity for the abasic site and may attach irreversibly to the site when deprived of $Mg^{2+}$ ions. APE1 may be fluorescently-labeled for optical detection, however colorimetric or radioactive tags may also be used.

FIGS. 2A and 2B are schematic illustrations of a Ricin and/or SLT activity assay in accordance with embodiments of the present invention. Although a Ricin/SLT activity assay is shown, any toxin that causes depurination of a DNA or RNA substrate may be detected and/or quantified in other examples. FIG. 2A illustrates an overall mechanism of the activity assay. A sarcinricin loop 201 is shown including adenine residue 202 at position 4324 (A4324). The residue 202 may be attacked by Ricin and/or SLT causing depurination in the loop 201 resulting in an abasic site 204. This process, and thus the activity of Ricin and/or SLT, may be detected by addition of fluorescently labeled APE 205, which binds to the abasic site 204 irreversibly in the absence of $Mg^{2+}$.

In FIG. 2B(1), a sample 206 is shown including Ricin and/or SLT, e.g., Ricin and/or SLT 203. Samples used in Ricin and/or SLT activity assays described herein may or may not include Ricin, as assay may be used to detect the presence of Ricin and/or SLT and/or to quantify the amount of active Ricin and/or SLT present in a sample. The sample may include any of variety of fluids, including biological fluids such as serum.

FIG. 2B(2) is a schematic illustration of a suspension of sedimentation particles in accordance with an embodiment of the present invention. In FIG. 2B(2), a particle suspension 207 may include sedimentation particles (e.g., bead 208) and labeling agent (e.g., fluorescently labeled APE 1 205). As has been described above, the sedimentation particles may have sarcin-ricin loop 201 on their surface. The fluorescently labeled APE 1 205 may be configured to attach to an abasic site left after an attack from a toxin. As shown in FIG. 2B, the sample and the particle suspension may be mixed (e.g. by vortexing, pipetting, and/or sonication).

FIG. 2B(3) is a schematic illustration of attack of Ricin and/or SLT 203 on residue 202 at position A4324 in a sarcin-ricin loop 201 conjugated to the surface of bead 208. This attack results in formation of abasic site 204.

FIG. 2B(4) is a schematic illustration of complexes that may be formed in the mixture. The fluorescently labeled APE 1 205 may form a complex with the abasic-site 204 (in the sarcin-ricin loop 201) containing bead 208. Any number of complexes may be formed on the bead, with four shown in FIG. 2B(4). The mixture 209 may be layered over a density medium 210. The density media 210 is generally a liquid which may have a density lower than a density of sedimentation particles (e.g. beads) used in an assay and higher than a density of the fluid sample. The density media may generally be implemented using a fluid having a density selected to be in the appropriate range—lower than a density of the beads used to conduct an assay and higher than a density of the fluid sample. In some examples, a fluid sample may be diluted for use with a particular density media. The density media may include a Percoll™ solution, available from GE lifesciences, which may contain various additives. Examples of density media may include 95% Percoll™. Generally, viscosity and density may be adjusted by changing a composition of the media. The mixture 209 may be introduced into a fluidic feature 211 (e.g. microfluidic device, including those described herein, vial or other fluid-containing structure) such that the mixture 209 is next to or on top of the density media 210. Before or after layering, the mixture may be incubated to allow for formation of complexes. The density media may have a density that is greater than the sample but less dense that the sedimentation particles (e.g. bead 208). Sedimentation forces (e.g. centrifugal or gravitational) may be applied to the mixture. For example, a disk containing the fluidic feature containing the mixture may be spun to apply a centrifugal force.

FIG. 2B(5) is a schematic illustration of the fluidic feature following sedimentation. The sedimentation particles, including the bead 208 may be transported through the density media 210 responsive to the sedimentation forces and may form a pellet 212 at an end of the structure. As the sedimentation particles (e.g. beads) are transported through the density media, the flow may wash the particles, removing unbound material and improving the detection of the assay. Sample and any unbound label may not be transported through the density media 210 and may remain within the sample or at an interface between the density media and the sample.

Figure 3:
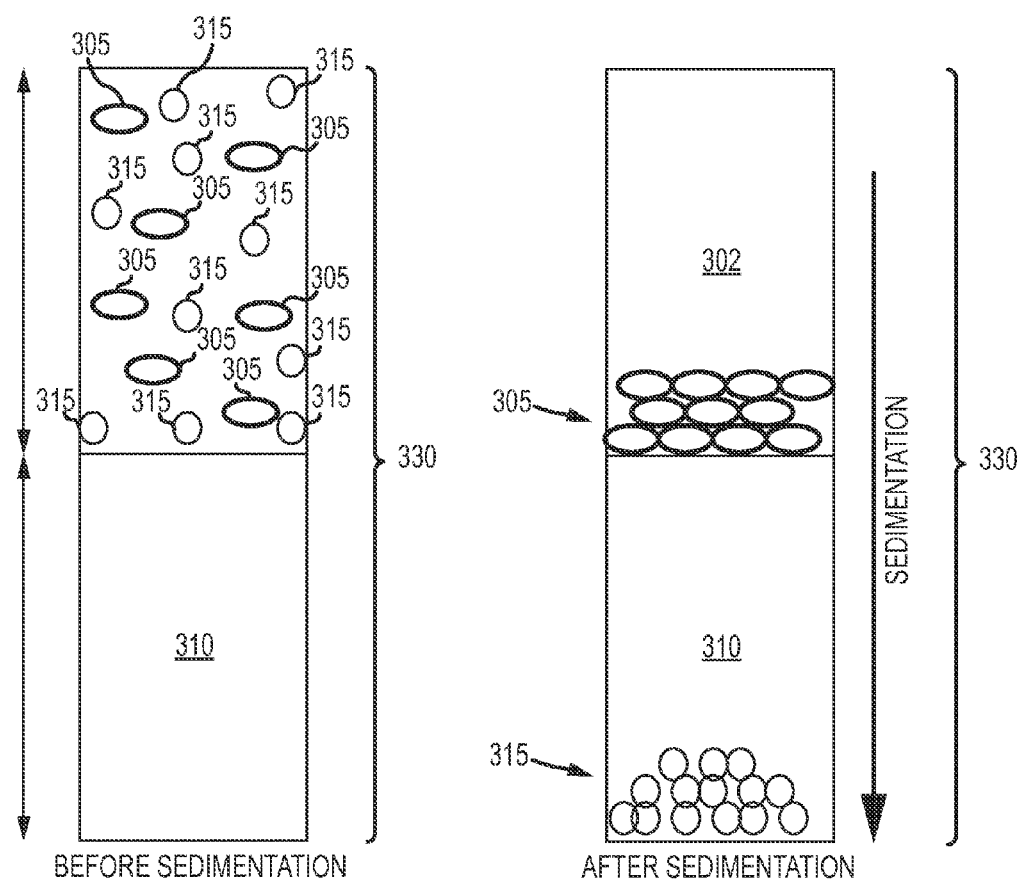
FIG. 3 is a schematic illustration of a detection region of a fluid-holding device before and after sedimentation in accordance with an embodiment of the present invention.

In some examples, it may be of interest to directly measure active toxin levels in whole blood samples. FIG. 3 is a schematic illustration of a detection region 330 of a fluid-holding device (e.g., microfluidic device, disk) before and after sedimentation in accordance with an embodiment of the present invention. A whole blood sample 302 including red blood cells 305 and silica beads 315 may be introduced to the detection region 730 next to or over a density media 310. Although not shown in FIG. 3, the silica beads 315 may be modified with a substrate such as a sarcin-ricin loop or MHC II conjugated to the beads. This may lead to effective binding of an active toxin in the fluid sample 302 to form complexes or formation of complexes responsive to the presence of active toxins, as generally described herein. The density media 310 may have a density greater than the red blood cells 305, but less than that of the beads 315.

Generally, blood cells may have a density less than or equal to 1.095 g/cc, and the silica beads may have a density of about 2.05 g/cc. Accordingly, the density media 510 may have a density of between about 1.095 g/cc and 2.05 g/cc. In one example, the density media 510 has a density of 1.11 g/cc.

Sedimentation described herein may occur under the influence of a natural gravitational force, such as by allowing the assay to sit, unpowered, under the influence of a gravitational force. Sedimentation may also occur using centrifugal force, such as by spinning a microfluidic disk. For examples, silica beads on the order of 10-30 microns in diameter may sediment in minutes under a normal gravitational force. Following sedimentation, as shown in FIG. 3, the blood cells 305 may be prohibited from transport through the denser density media 310. The beads 315, however, may be transported through the density media 310 to a detection location, and active toxin may be tested using signal from a labeling agent, as described above.

Ricin and/or SLT activity assays conducted in accordance with embodiments of the present invention may accordingly separate interfering matrix components from the active Ricin and/or SLT in complexes. For example, inactive Ricin and/or SLT or other components in a sample may not cause depurination of the DNA (or RNA) substrate covalently linked to surface of silica beads. The lack of depurination may prevent attachment of fluorescently labeled APE1 to the substrate, and, thus, formation of substrate-label complexes. Other components and inactive Ricin and/or SLT may not cause formation of complexes, and may not travel through the density media due to the density of the particle being less than the media. Accordingly, sensitivity of determination of active Ricin and/or SLT may be improved through use of sedimentation assays described herein. The sensitivity of detection and/or quantification may also be improved relative to standard techniques by determination and/or quantification of the active Ricin and/or SLT in the sample, concentration in a pellet, and/or enhancement of fluorescent signal during transport through the density medium. Still further Ricin and/or SLT assays in accordance with the present invention may be performed in a relatively short period of time.

Examples of the present invention include assays for detection and/or quantification of active Staphylococcal enterotoxin B (SEB). SEB is a protein toxin and generally functions as a superantigen. SEB may be responsible for a number of extensive pathophysiological changes in humans and mammals and may trigger an excessive cellular immune response leading to toxic shock. SEB may be called a superantigen because it interacts with the immune system to produce an excessive response, activate a very high percentage of T-cells, which may lead to toxic shock. It is approximately 24-29 kDa in size. It causes non-specific cross linking of major histocompatibility complex (MHC) II and T cell receptors (TCR). This may cause rapid proliferation of T-cells and production of cytokines, which then lead to significant inflammation. Exposure to SEB may cause severe diarrhea, vomiting, cramping, inflammation of skin, eye, fever, headache, and even toxic shock.

In an example of SEB activity assay described herein, crosslinking of MHC II and T-cell receptors by SEB is used to determine its activity. For example, an immortalized T-cell line, such as Jurkat cells, which express T-cell receptors on the cell surface may be used to cross-link with MHC II via SEB. In one embodiment, fixed Jurkat cells may be used, making them readily available and precluding maintenance of live cell cultures prior to the assay. In one embodiment, the Jurkat cells used may be stained by acridine orange. The MHC II may be conjugated to 1 μm silica microparticles. In presence of SEB a complex may form between the Jurkat cells and MHC II conjugated to silica microparticles, through SEB. These complexes may be separated from unbound Jurkat cells and MHC II-silica microparticles conjugates by using a density media denser than the Jurkat cells.

In an example of a SEB activity sedimentation assay, when Jurkat cells and silica microparticles conjugated to MHC II are placed together in the presence of SEB, the dense microparticles may act as a sink, and drive the Jurkat cells down through the density media by sedimentation force (e.g. gravitational or centrifugal force). In the absence of active SEB, the Jurkat cells may stay above the density media.

Figure 4:
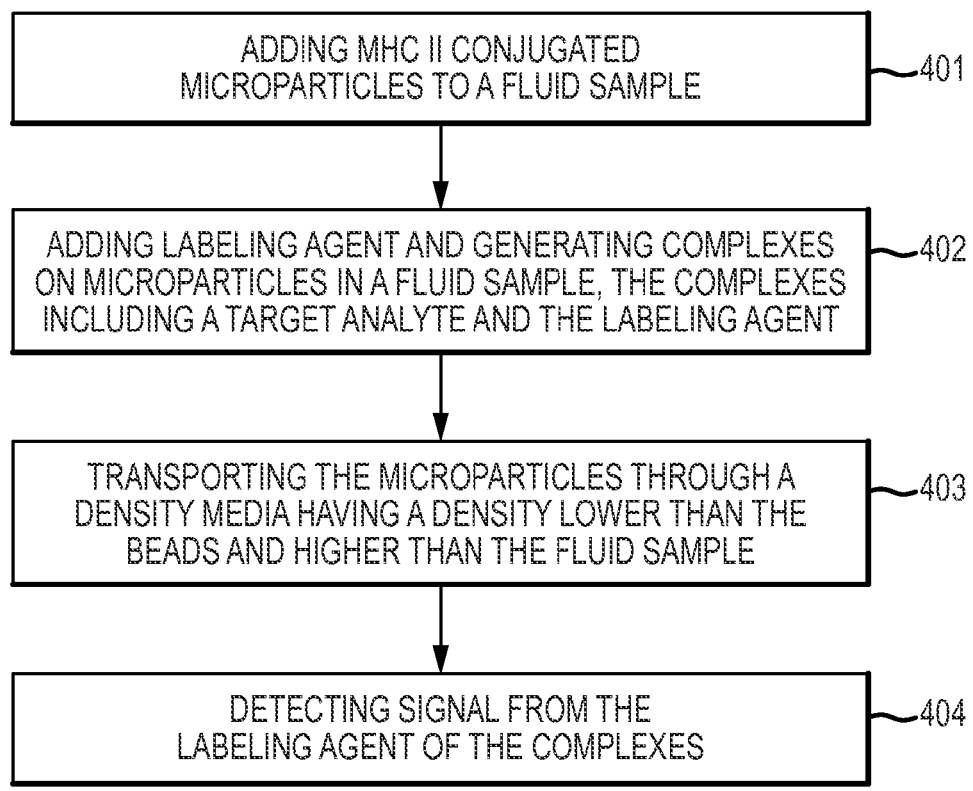
FIG. 4 is a flowchart illustrating method of conducting a SEB activity assay in accordance with embodiments of the present invention.

FIG. 4 is a flowchart illustrating a method for conducting SEB activity assay in accordance with embodiments of the present invention. In block 401, MHC II conjugated to microparticles is added to a fluid sample. In block 402 a labeling agent, stained Jurkat cells, expressing TCR, attaches to MHC II via SEB forming a complex. The complexes may be generated on sedimentation particles (e.g., beads) in a fluid sample. The complexes may include the substrate targeted by the toxin and the labeling agent. Block 402 may be followed by block 403. In block 403, the sedimentation particles, e.g., the complexes, may be transported through a density media having a lower density than the beads but higher than the fluid sample. Gravitational forces generated naturally or by centrifugation may be used to transport the beads through the density media. The sedimentation particles accordingly may sediment out of the fluid sample, forming a concentrated pellet. Block 403 may be followed by block 404. In block 404, a signal may be detected from the labeling agent of the complexes. In some examples, by separating the sedimentation particles from the sample fluid using sedimentation forces, the beads are also concentrated, which may eliminate or reduce a need for amplification of the labeling agent.

Figure 5A:
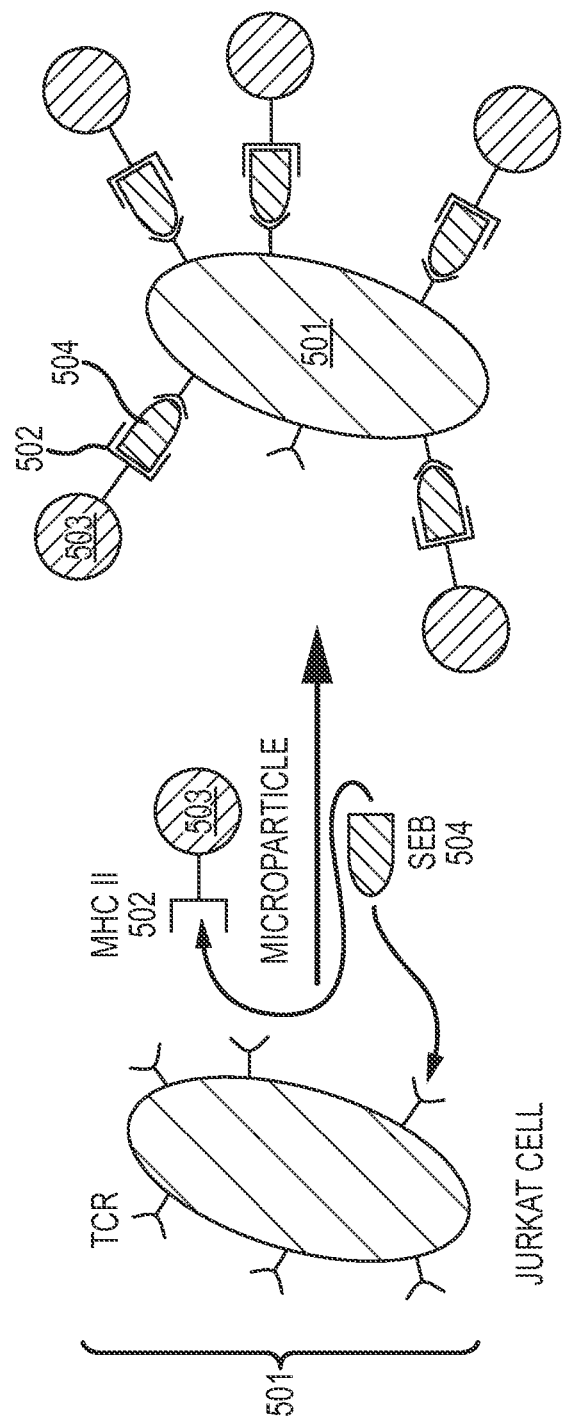
FIGS. 5A and 5B are schematic illustrations of a SEB activity assay in accordance with embodiments of the present invention.
Figure 5B:
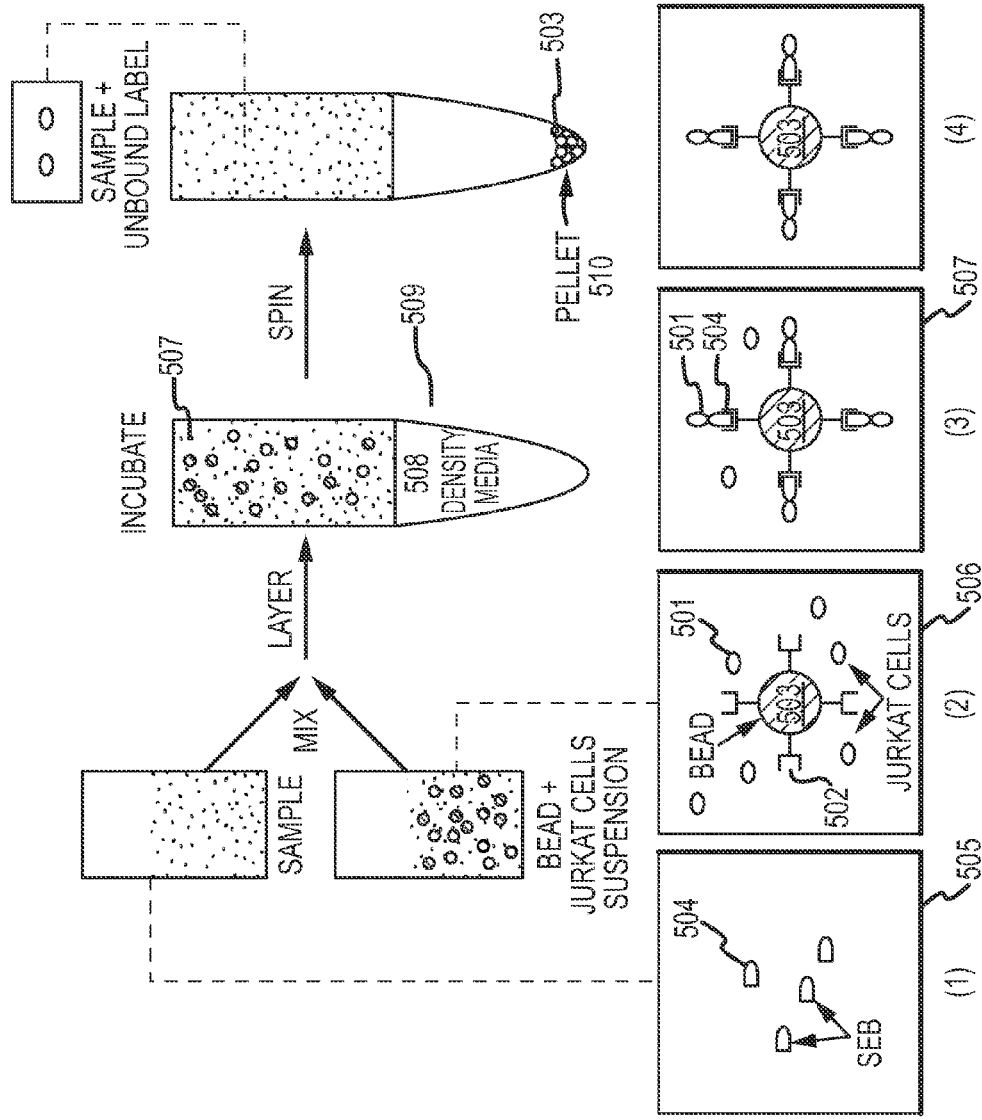

FIGS. 5A and 5B are schematic illustrations of a SEB activity assay in accordance with embodiments of the present invention. Although a SEB activity assay is shown, any toxin that causes activation of T-cell receptors by cross-linking with MHC II may be detected and/or quantified in other examples. FIG. 5A illustrates an example overall mechanism of the activity assay. MHC II 502 conjugated microparticle 503 (e.g. bead) is shown. Stained Jurkat cells 501, expressing T-cell receptors (TCR), may be used as labeling agent. In the presence of SEB 504, a complex may be formed between stained Jurkat cells 501 and MHC II 502 conjugated microparticle 503 cross-linked via SEB 504.

FIGS. 5B(1)-(4) are schematic illustrations of a SEB activity assay in accordance with embodiments of the present invention. Although a SEB activity assay is shown, as mentioned above, any toxin that crosslinks TCR with MHC II may be detected and/or quantified in other examples. In FIG. 5B(1), a sample 505 is shown including SEB, e.g. SEB 504. Samples used in SEB activity assays may or may not include SEB, as the assay may be used to detect the presence of SEB and/or to quantify the amount of active SEB present in a sample.

FIG. 5B(2) is a schematic illustration of a suspension of sedimentation particles in accordance to an embodiment of the present invention. In FIG. 5B(2), a particle suspension 506 may include sedimentation particles (e.g. bead 503) and labeling agents (e.g. stained Jurkat cells 501 expressing TCR). As has been described above, the sedimentation particles may be conjugated to MHC II 502. The stained Jurkat cells 501 expressing TCR may be stained by acridine orange. As shown in FIG. 5, the sample and the particle suspension may be mixed (e.g. by vortexing, pipeting, and/or sonication).

FIG. 5B(3) is a schematic illustration of complexes that may be formed in the mixture. SEB 504 may form a cross-link between stained Jurkat cells 501 expressing TCR and MHC II 502 conjugated to microparticles (e.g. beads 503) resulting in a complex. Any number of complexes may be formed on the bead, with four shown in FIG. 5B(3). The mixture 507 may be layered over a density media 508. The density media 508 is generally a liquid which may have a density lower than a density of sedimentation particles (e.g. beads) used in an assay and higher than a density of the fluid sample. The density media may generally be implemented using a fluid having a density selected to be in the appropriate range—lower than a density of the beads used to conduct an assay and higher than a density of the fluid sample. In some examples, a fluid sample may be diluted for use with a particular density media. An example of a suitable density media is Percoll™, available from GE Lifesciences. Particular densities may be achieved by adjusting a percentage of Percoll™ in a solution. More generally, viscosity and density may be adjusted by changing a composition of the media. The mixture 507 may be introduced into a fluidic feature 509 (e.g. microfluidic device, including those described herein, vial, or other fluid-containing structure) such that the mixture 507 is next to or on top of the density media 508. Before or after the layering, the mixture may be incubated to allow for formation of the complexes. The density media may have a density that is greater than the sample but less dense than the sedimentation particles (e.g. bead 503). Sedimentation forces (e.g. centrifugal or gravitational) may be applied to the mixture. For example, the feature containing the mixture may be spun to apply a centrifugal force.

FIG. 5B(4) is a schematic illustration of the fluid containing structure following sedimentation. The sedimentation particles, including the bead 503 may be transported through the density media 508 responsive to the sedimentation forces and may form a pellet 510 at an end of the structure. As the sedimentation particles (e.g. beads) are transported through the density media, the flow may wash the particles, removing unbound material and improving the detection of the assay. Sample and any unbound label may not be transported through the density media 508 and may remain within the sample or at an interface between the density media and the sample.

SEB activity assays conducted in accordance with embodiments of the present invention may accordingly separate interfering matrix components from the active SEB in the complexes. For example, inactive SEB or other components in a sample may not cause cross-linking of cells expressing TCR and MHC II conjugated to silica beads. The lack of cross-linking will prevent attachment of stained cells to the substrate, and, thus, formation of substrate-label complexes. Other components and inactive SEB may not cause formation of complexes, and may not travel through the density media due to the density of the interfering components being less than the media. Accordingly, sensitivity of determination of active SEB may be improved. The sensitivity of detection and/or quantification may also be improved relative to standard techniques by determination of only the active SEB in the sample, concentration in a pellet, and/or enhancement of fluorescent signal during transport through the density medium. Still further SEB assays in accordance with the present invention may be performed in a relatively short period of time.

In some embodiments, methods described herein may be implemented using a microfluidic disk. FIG. 6 is a schematic illustration of a microfluidic disk 600 arranged in accordance with embodiments of the present invention. The microfluidic disk 600 may include a substrate 610 which may at least partially define regions of assay areas 620, 621, 622, and 623. The microfluidic disk 600 may include a fluid inlet port 625 in fluid communication with the assay areas 620, 621, 622, and 623. Each assay area my include any of a variety of fluidic features and components, including but not limited to, channels, chambers, valves, pumps, etc. As show in FIG. 6, each assay area includes a mixing chamber and a detection region connected by a channel, which may contain a valve. During operation, fluids including sample liquids, density media, and/or beads suspended in a fluid, may be transported using centrifugal force from an interior of the microfluidic disk 600 towards a periphery of the microfluidic disk 600 in a direction indicated by an arrow 630. The centrifugal force may be generated by rotating the microfluidic disk 600 in the direction indicated by the arrow 635, or in the opposite direction.

The substrate 610 may be implemented using any of a variety of suitable substrate materials. In some embodiments, the substrate may be a solid transparent material. Transparent plastics, quartz, glass, fused-silica, PDMS, PMMA and other transparent substrates may be desired in some embodiments to allow optical observation of sample within the channels and chambers of the disk 600. In some embodiments, however, opaque plastic, metal or semiconductor substrates may be used. In some embodiments, multiple materials may be used to implement the substrate 610. The substrate 610 may include surface treatments or other coatings, which may in some embodiments enhance compatibility with fluids placed on the substrate 610. In some embodiments surface treatments or other coatings may be provided to control fluid interaction with the substrate 610. While shown as a round disk in FIG. 46 the substrate 610 may take substantially any shape, including square.

In some embodiments, as will be described further below, the substrate 610 may itself be coupled to a motor for rotation. In some embodiments, the substrate may be mounted on another substrate or base for rotation. For example, a microfluidic chip fabricated at least partially in a substrate may be mounted on another substrate for spinning In some examples, the microfluidic chip may be disposable while the substrate or base it is mounted on may be reusable. In some examples, the entire disk may be disposable. In some examples, a disposable cartridge including one or more microfluidic channels may be inserted into disk or other mechanical rotor that forms part of a detection system.

The substrate 610 may generally at least partially define a variety of fluidic features. The fluidic features may be microfluidic features. Generally, microfluidic, as used herein, refers to a system, device, or feature having a dimension of around 1 mm or less and suitable for at least partially containing a fluid. In some embodiments, 500 µm or less. In some embodiments, the microfluidic features may have a dimension of around 100 µm or less. Other dimensions may be used. The substrate 410 may define one or more fluidic features, including any number of channels, chambers, inlet/outlet ports, or other features.

Microscale fabrication techniques, generally known in the art, may be utilized to fabricate the microfluidic disk 600. The microscale fabrication techniques employed to fabricate the disk 600 may include, for example, embossing, etching, injection molding, surface treatments, photolithography, bonding and other techniques.

A fluid inlet port 625 may be provided to receive a fluid (e.g. sample) that may be analyzed using the microfluidic disk 600. The fluid inlet port 625 may have generally any configuration, and a fluid sample may enter the fluid inlet port 625 utilizing substantially any fluid transport mechanism, including pipetting, pumping, or capillary action. The fluid inlet port 425 may take substantially any shape. Generally, the fluid inlet port 625 is in fluid communication with at least one assay area, and may be in fluid communication with multiple assay areas 620-623 in FIG. 4. Generally, by fluid communication it is meant that a fluid may flow from one area to the other, either freely or using one or more transport forces and/or valves, and with or without flowing through intervening structures.

Figure 6:
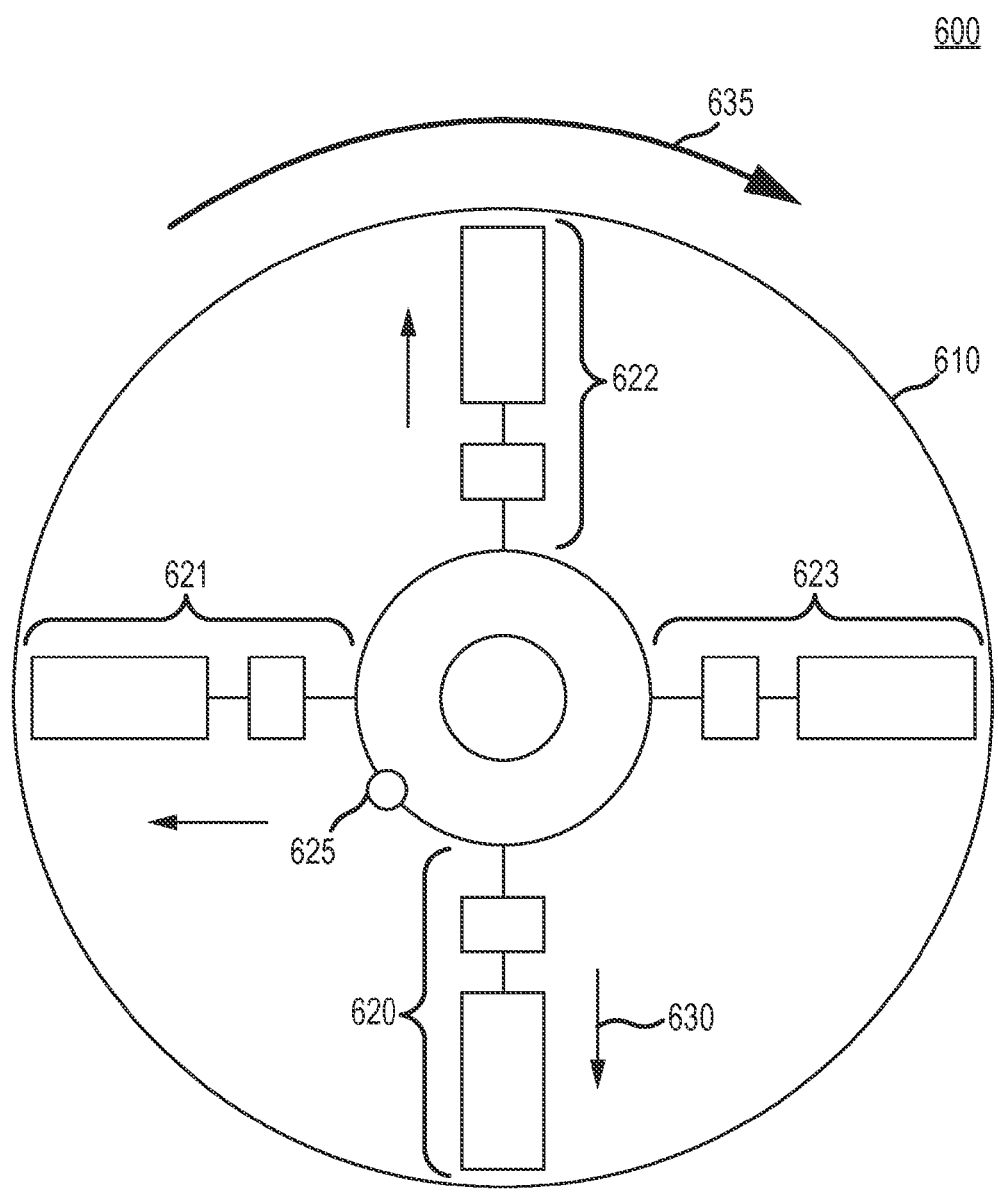
FIG. 6 is a schematic illustration of a microfluidic disk arranged in accordance with embodiments of the present invention.

The assay area 620 generally may include one or more channels in fluid communication with the fluid inlet port 625. Although four assay areas 620-623 are shown in FIG. 6, generally any number may be present on the microfluidic disk 600.

As the microfluidic disk 600 is rotated in the direction indicated by the arrow 635 (or in the opposite direction), a centrifugal force may be generated. The centrifugal force may generally transport fluid from the inlet port 625 into one or more of the assay areas 620-623.

Accordingly, the microfluidic disk 600 may be used to perform assays described herein. Centrifugal forces may be used to generate sedimentation forces described herein. In other examples, however, gravity may be used to generate sedimentation forces, and assays described herein may be conducted in a vial or other container.

FIGS. 7A-C are schematic illustrations of an assay area 620 of a microfluidic disk in accordance with an embodiment of the present invention. The assay area 620 includes a channel 710 in fluid communication with the fluid inlet port 625. The channel 710 may be in fluid communication with a detection region 730. Another reservoir 735 may be in fluid communication with the detection region 730 via a channel 740, which may include or serve as a valve. The detection region 730 may be implemented as a fluidic chamber, channel, or reservoir, and detection may occur at an end of the region. In other examples, detection may not occur in the detection region 730, but the sample may be transported elsewhere for detection.

The detection region 730 and reservoir 735 may generally be implemented using any size and shape, and may contain one or more reagents including solids and/or fluids which may interact with fluid entering and/or exiting the features.

The detection region 730 may be configured to contain a density media. Constituents of an appropriate density media are explained previously. In some embodiments, the density media may include a detergent, such as Tween 20. The detergent may enhance a wash function of transport through the density media.

Sample, sedimentation particles, and labeling agent may first be mixed and/or incubated in the reservoir 735, as shown in FIG. 7A, then introduced at a selected time to the detection region 730 by operation of the valve 740. That is, a mixture of sample, sedimentation particles, and labeling agent suspension may be present in the reservoir 735 (for example by introducing the different components separately, or by loading a mixture containing all components into the reservoir 735). The valve 740 may be closed to contain the components in the reservoir 735 and allow the components to incubate to form complexes.

On opening the valve 740, as shown in FIG. 7B, the mixture including the sample, beads, and labeling agent, which may have formed complexes, may be introduced to the detection region 730. In some examples, the reservoir 735 may not be provided, and the mixture may be loaded directly into the detection region 730, which may be a channel or chamber. Detection may take place at an end of the detection region 730. The detection region 730 may further have a tapered or other shape at the end of the detection region 730.

The detection region 730 may be a channel or chamber and may vary in configuration in accordance with the detection technique employed, as will be described further below. The detection region 730 may generally be configured to allow for detection of a signal emitted by labeling agents in a complex. The complex may include active toxin and labeling agent in embodiments pertaining to toxin activity assays. In some examples, the complex may not itself include active toxin, but the complex may have formed due in part to the presence of active toxin in a sample. The complexes include sedimentation particles (e.g. microparticles, beads).

Centrifugal forces may generally be used to transport the mixture from the inlet port 725 toward the detection region 730. Additionally, centrifugal forces may be used to transport density media from the reservoir 735 to the detection region 730. In other examples, pressure-driven or other flow drivers may be used to load fluids into the device and transport the mixture to the detection region 730.

Incubation of sedimentation particles and labeling agents with the sample may take place within a microfluidic disk. Referring again to FIG. 7A, a fluid sample containing a target analyte, e.g. toxin, may be introduced to the inlet port 625 and provided to the reservoir 735 through the channel 710. Any of a variety of suitable fluid samples may be used including, but not limited to, whole blood, buffer solutions, serum, or other biological fluid samples. Generally, the fluid sample will include target analytes to be detected in accordance with embodiments of the present invention. The fluid sample may contain beads designed to form complexes responsive to the presence of active toxins and/or labeling agents designed to be incorporated into complexes responsive to the presence of active toxins. In other examples, the beads and/or label agents may be introduced to the fluid sample within the microfluidic disk 600. For example, a fluid containing the beads and/or label agents may be provided to a different inlet port in fluid communication with the channel 710 of FIG. 7. Either by mixing components or by providing a fluid containing the components, a sample fluid including beads, target analytes, and labeling agents, may be transported to the detection region 730 of FIG. 7. The transport of the sample fluid may occur through any type of transport mechanism, including centrifugal force, pressure-driven flow, pumping, or other mechanisms. In other examples, beads having capture agents on their surface may be incubated with target analyte and/or labeling agents prior to introduction to a microfluidic disk. In such an example, complexes may be formed on beads in a sample fluid prior to providing the sample fluid to the microfluidic disk.

Figure 7:
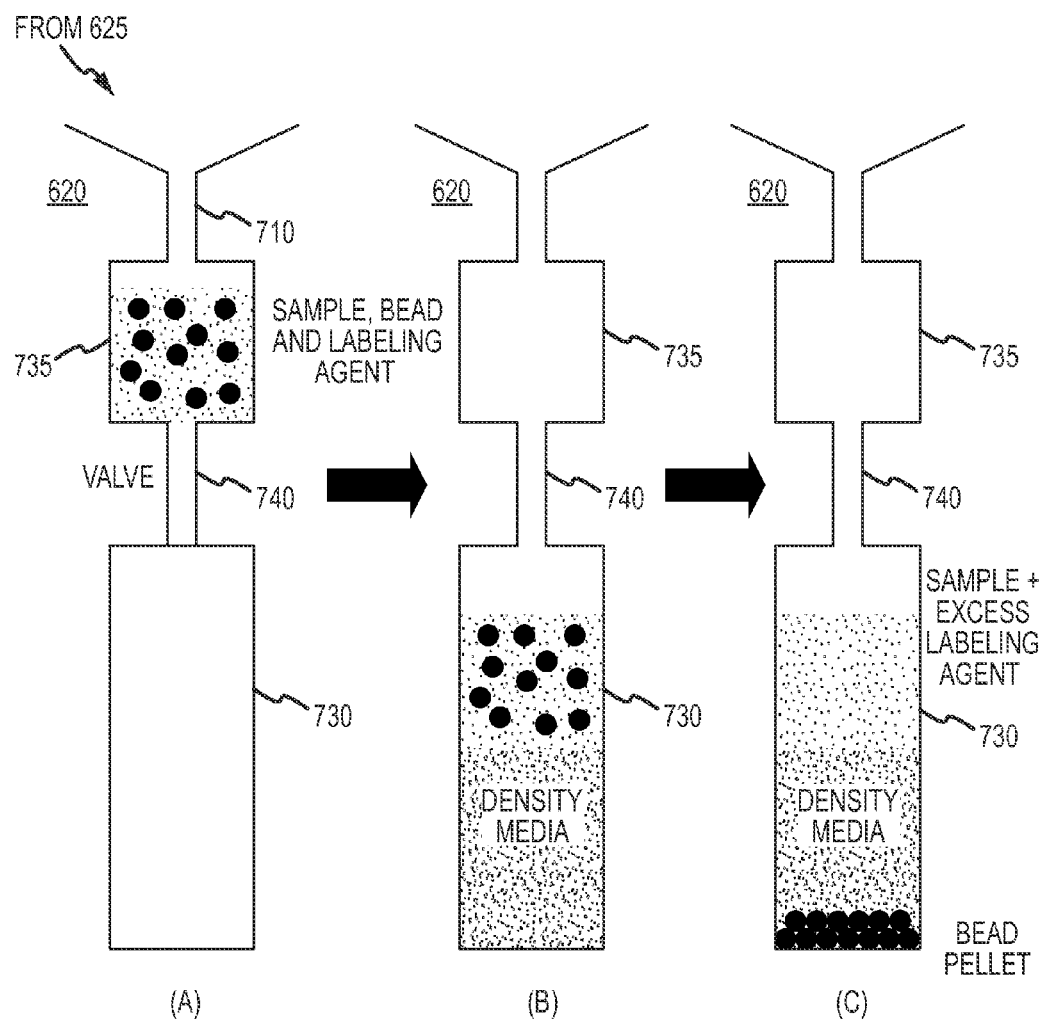
FIGS. 7A-C are schematic illustrations of an assay area 620 of microfluidic disk in accordance with an embodiments of the present invention.

The detection region 730 of FIG. 7 may contain density media, or density media may be transported into the detection region 730 from another location, such as from the reservoir 735. The channel 740 may have a width selected to serve as a valve, such that a spin rate over a threshold amount is required to initiate a flow of the density media from the reservoir 735 through the channel 740. In some examples, the channel 740 has a width selected such that any spin rates used to transport sample into the reservoir 735 is insufficient to transport the sample into the detection region 730. A spin rate of the microfluidic disk 600 may then be increased to initiate or enhance a flow of the sample from the reservoir 735 into the detection region 730. In this manner, the channel 740 may function as a valve. Other valve structures such as wax plugs that melt at a known temperature may be used in other examples.

Once the mixture of sample, bead, and labeling agent is in the detection region 730 above the density media (e.g. closer to the center of the disk), sedimentation forces may be used to transport the beads through the density media to form a bead pellet, as shown in FIG. 7C. If labeling agent is present on the bead, they may be detected in the concentrated pellet.

Accordingly, a sample fluid including: 1) beads; 2) target analytes; and 3) labeling agents may be transported to an interface with a density media and sedimentation forces used to transport the beads, along with any bound complexes, through the density media to form a pellet at the end of the detection region.

FIGS. 8-9 are schematic illustrations of the detection region 730 containing a sample fluid 801 and a density media 802 in accordance with an embodiment of the present invention. Components of the sample fluid 801 are shown for the purposes of illustration beneath the detection region 730 in FIG. 8. In FIGS., 8-9, schematic views of the sample components, and complex formation, are shown below the detection region view for ease of illustration. The sample fluid includes a plurality of beads, including bead 803 with surface modification (e.g., sarcin-ricin loop or MHC II). The sample fluid 801 further includes target analytes, such as active toxin 804, and labeling agent 805.

The sample fluid may then be incubated. FIG. 9 is a schematic illustration of the detection region 730 containing the sample fluid 801 and the density media 802 following an incubation period. Complexes may form on the bead 803. The target analyte 804 may bind to the bead 803 and labeling agent 805; alternatively, the target analyte may not bind to the bead 803 and labeling agent 805, but may cause formation of complexes responsive to the presence of analyte (active toxins) and/or label agents designed to be incorporated into complexes responsive to the presence of the target analyte (not shown in FIGS. 8 and 9). Some unbound, free labeling agents, however, remain in the sample fluid 801. At times a little to no centrifugal force may be provided to aid incubation. Additionally, in some examples, a region of the microfluidic disk containing the sample fluid may be headed to enhance incubation. In this manner, complexes may be formed on the beads. As understood in the art, the amount of labeling agent bound to complexes on the beads will be generally proportional to the amount of target analyte in the fluid sample. Any number of complexes may be formed on the beads, with three complexes shown on the bead 803 in FIG. 9.

The beads may then be transported through the density media. The beads are transported through the density media using centrifugal force, such as that which may be applied by motor, described further below. Following a period of centrifugal force, the beads may be concentrated in a detection location. FIG. 10 is a schematic illustration of the detection region 730 following transport of beads through the density media. The fluid sample 801 may remain separated from the density media 802, as the density media 802 may have density higher than that of the sample fluid 801. Free, unbound labeling agent, may remain in the sample fluid 801. Beads 803, including complexes, may be transported through the density media 802 to a detection location 806. Beads at the detection location 806 are shown for purposes of illustration under the detection region 730 in FIG. 10. The bead 803 includes complexes containing target analyte 804 and labeling agent 805; alternatively, the bead 803 may include complexes formed in response to the presence of active toxins and/or label agents designed to be incorporated into complexes responsive to the presence of the target analyte (not shown in FIGS. 8 and 9) However, unbound labeling agent may not be found in the detection location 806. As shown in FIGS. 8-10, centrifugal force may accordingly be used to separate complexed beds from a sample fluid and to concentrate the complexed beads. In this manner, the need for additional assay may be reduced or eliminated. Signal from labeling agent of the concentrated beads may be detected from the detection location 806 using, for example, the detection module examples described below.

Figure 11:
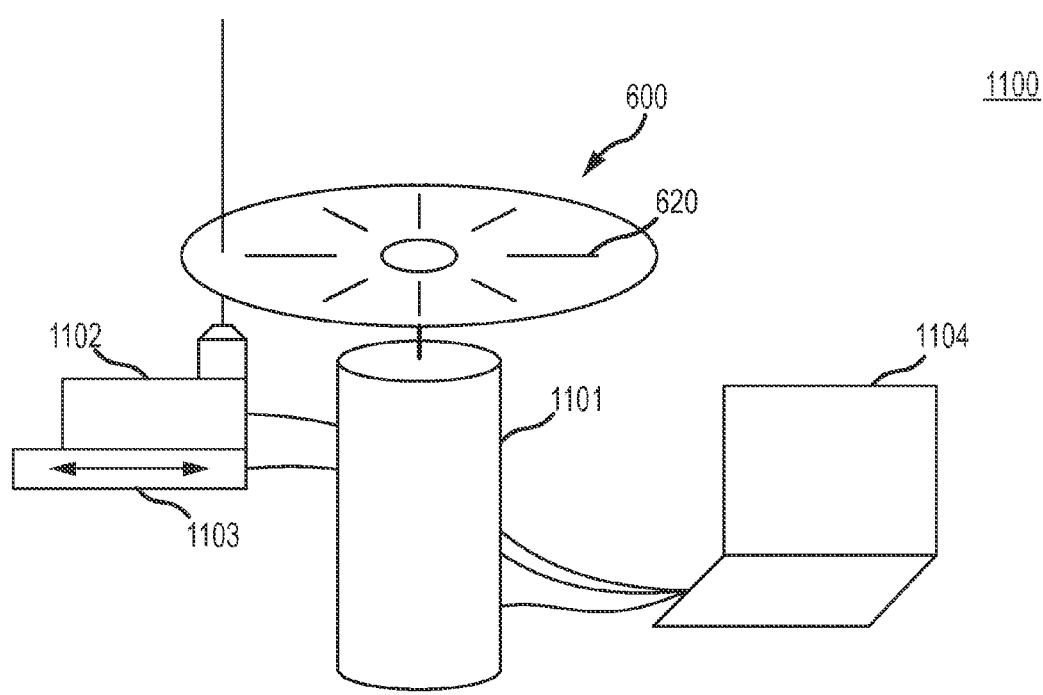
FIG. 11 is a schematic illustration of a system according to an embodiment of the present invention.

FIG. 11 is a schematic illustration of a system according to an embodiment of the present invention. The system 1100 may include the disk 600 of FIG. 6 with one or more assay areas 620. A motor 1101 may be coupled to the disk 600 and configured to spin the disk 600, generating centrifugal forces. A detection module 1102 may be positioned to detect signal from labeling agents in a detection region of the assay area 620. An actuator 915 may be coupled to the detection module 1102 and configured to move the detection module along the detection region in some examples. A processing device 1104 may be coupled to the motor 1101, the detection module 102, and/or the actuator 1103, and may provide control signals to those components. The processing device 1104 may further receive electronic signals from the detection module 1102 corresponding to the labeling agent signals received from the detection module 1102. All or selected components shown in FIG. 11 may be housed in a common housing in some examples. Microfluidic disks, which may be disposable, may be placed on the motor 1101 and removed, such that multiple disks may be analyzed by the system 1100.

The motor 1101 may be implemented using a centrifugation and/or stepper motor. The motor 1101 may be positioned relative to the detection module 1102 such that, when the disk 600 is situated on the motor 1101, the disk is positioned such that a detection region of the assay area 620 is exposed to the detection module 1102.

The detection module 1102 may include a detector suitable for detecting signal from labeling agents in complexes that may include labeling agent. In toxin activity assays (e.g., Ricin, SLT, and/or SEB) assays, the complexes may include active toxin and labeling agent or may form in response to the presence of an active toxin and/or label agent designed to be incorporated into complexes responsive to the presence of active toxin The complexes may be formed on the surface of one or more sedimentation particles (e.g., beads), as described further below. The detector may include, for example, a laser and optics suitable for optical detection of fluorescence from fluorescent labeling agents. The detection module may include one or more photomultiplier tubes. In other examples, other detectors, such as photodiodes or CCD cameras, may be used. The actuator 1101 may move the detector in some examples where signal may be detected from a variety of locations of the microfluidic disk 600.

The processing device 1104 may include one or more processing units, such as one or more processors. In some examples, the processing device 1104 may include a controller, logic circuitry, and/or software for performing functionalities described herein. The processing device 1104 may be coupled to one or more memories, input devices, and/or output devices including, but not limited to, disk drives, keyboards, mice, and displays. The processing device may provide control signals to the motor 1101 to rotate the disk 600 at selected speeds for selected times. The processing device may provide control signals to the detection module 1102, including one or more detectors and/or actuators, to detect signals from the labeling agents and/or move the detector to particular locations. The processing device may develop these control signals in accordance with input from an operator and/or in accordance with software including instructions encoded in one or more memories, where the instructions, when executed by one or more processing units, may cause the processing device to output a predetermined sequence of control signals. The processing device 1104 may receive electronic signals from the detection module 910 indicative of the detected signal from labeling agents. The processing device 1104 may detect a target analyte and/or calculate a quantity of a target analyte in a fluid sample based on the signals received from the detection module 1102. Accordingly, the processing device 1104 may perform calculations in accordance with software including one or more executable instructions stored on a memory causing the processing device to perform the calculations. Results may be stored in memory, communicated over a network, and/or displayed. It is to be understood that the configuration of the processing device 1104 and related components is quite flexible, and any of a variety of computing systems may be used including server systems, desktops, laptops, controllers, and the like.

Having described examples of micro fluidic disks and systems in accordance with embodiments of the present invention, methods for conducting assays will now be described. Some discussion will also be provided regarding mechanisms for sedimentation and centrifugation. The discussion regarding mechanisms is provided as an aid to understanding examples of the present invention, but is in no way intended to limit embodiments of the present invention. That is, embodiments of the present invention may not employ the described mechanism.

Sedimentation of spheres may occur within a viscous fluid under the influence of a gravitational field (which may be natural or induced by centrifugation). The settling velocity of approximately spherical particles may be described by Stoke's flow equations:

$$V_s = \frac{2}{9}\frac{(\rho_p - \rho_f)}{\mu}gR^2;$$

where Vs is the sedimentation velocity, μ is the fluid viscosity, ρp is the density of the particle, ρf is the density of the fluid, g is acceleration due to effective gravity, and R is the particle radius. Note that sedimentation rate scales with the square of particle radius and therefore a small difference in radius may form a basis for separation of particles in some examples, as they may sediment at a different rate. There is also a linear dependence of sedimentation rate with the difference in density between the particle and the surrounding fluid, which may also be an effective mechanism for separation. Accordingly, beads or other particles may be separated according to their density and/or radius based on different sedimentation velocities. Separation of particles using these principles may be referred to as "rate zonal centrifugation."

For nanometer scale particles, such as active toxins, gravitational forces may act in conjunction with Brownian diffusion, but neither will generally cause motion of these nanometer scale particles over significant distances during typical centrifugal conditions (<100,000 g). Accordingly, beads with affinity for active toxins, due to surface modifications, may be used to separate active toxins from a fluid sample containing mixture of other small molecules. By capturing active toxin on the bead surface, and separating the beads from the remaining sample using sedimentation (e.g. centrifugal or gravitational) forces, the need for wash steps may be reduced or eliminated, because unbound labeling agents and/or other molecules may be dissociated from the beads by fluid flow.

EXAMPLE 1

For ricin and/or shiga-like toxin activity assay, a sample may be incubated with microparticle-conjugated stem-loop substrates for 20 or 240 min in 10 mM potassium citrate at pH 4.0. To this suspension, fluorescently labeled APE1 may be added to a final concentration of 100 nM, as well as PBS (pH 7.4) with between 50 mM EDTA and 250 mM EDTA. The fluorescent label may be an organic dye, such as Alexa Fluor 647 from Molecular Probes, a quantum dot, such as QDot 585 from Molecular Probes, dye-loaded latex particles, such as 10 nm FluoSpheres from Life Technologies. The suspension may be allowed to react for 20 min. After incubation, 4 μL of the suspension may be added to a channel pre-loaded with density medium. Density medium may be 95% Percoll and 5% (v/v) concentrate of additives in distilled water containing 50 mM sodium phosphate, 125 mM EDTA, 0.01% Tween 20 (w/v) and 100 mM sodium chloride. The channel may be spun at 8000 rpm for 45 s, transporting the microparticles through the density medium to form a pellet in a detection area. The pellet may be imaged using a fluorescent microscope.

FIG. 12 shows a dose response curve generated using serial dilutions of Ricin. Concentration of ricin in picomoles (pM) is plotted on the X-axis against the corresponding fluorescence intensity measured in relative fluorescence units (RFU) on the Y-axis. In assay where a sample containing Ricin was incubated with a labeling agent and modified beads for 20 minutes, the lowest concentration of ricin that could be detected was 780 pM. However, in an assay where the incubation period was increased to 240 minutes, the lowest concentration of ricin that could be detected was 13 pM. As may be seen in FIG. 12, the fluorescence intensity detected increased with increase in concentration of ricin.

FIG. 13 shows a dose response curve generated using serial dilutions of SLT. Concentration of SLT in nanomoles (nM) is plotted on the X-axis against the corresponding fluorescence intensity measured in relative fluorescence units (RFU) on the Y-axis. As may be seen in FIG. 13, the fluorescence intensity detected increased with increase in concentration of SLT.

EXAMPLE 2

For SEB activity assay, MHC II may be immobilized to 1 μm carboxylic acid functionalized microparticles. Jurkat cells may be fixed in ice-cold methanol for 5 min, washed in PBS, and stained with 100 μM acridine orange for 10 min. Following which the cells may be washed in PBS and resuspended to a concentration of $3\times10^7$ cells/mL. To 7 μL of a 5% solid suspension of MHC II-conjugated microparticles, 7 μL of SEB toxin and 1 μL of stained Jurkat cells may be added.

Hela cells may be used as a negative control. HeLa cells may be treated with trypsin and EDTA for 5 min at 37° C., washed with PBS, fixed in ice-cold methanol for 5 min, stained with 100 100 μM acridine orange for 10 min, and resuspended at a concentration of $3.8 \times 10^7$ cell/mL. To 7 μL of a 5% solids suspension of MHC II-conjugated microparticles 7 μL of SEB toxin and 1 μL of HeLa cells may be added.

The channel may be spun at 8000 rpm for 45 s, transporting the microparticles through the density medium to form a pellet in a detection area. Resultant bead pellets (for both Jurkat cells and, negative control, HeLA cells) may be imaged on a fluorescent microscope using 488 nm excitation and 525 nm emission.

Figure 14:
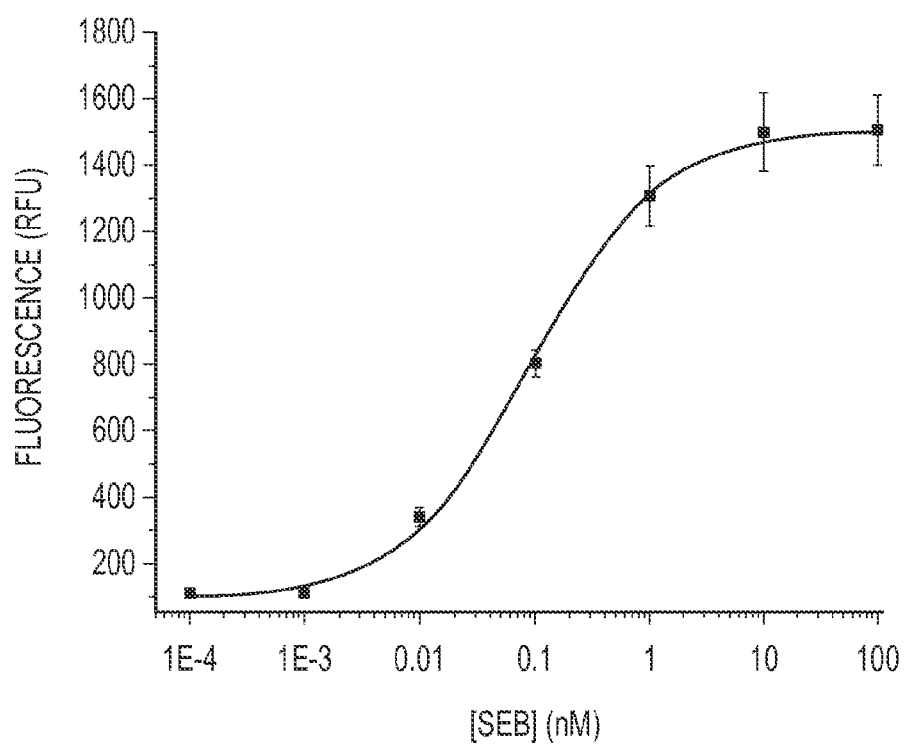
FIG. 14 shows a dose response curve generated using serial dilutions of SEB in accordance with embodiments of the present invention.

FIG. 14 shows a dose response curve generated using serial dilutions of SEB.

Concentration of SEB in nanomoles (nM) is plotted on the X-axis against the corresponding fluorescence intensity measured in relative fluorescence units (RFU) on the Y-axis. As may be seen in FIG. 14, the fluorescence intensity detected increased with increase in concentration of SEB.

What is claimed is:

1. A method of conducting a toxin activity assay, the method comprising:
   generating a plurality of complexes on a plurality of beads by action of an active toxin in a fluid sample, individual complexes of the plurality of complexes comprising a capture agent, and a labeling agent;
   transporting the plurality of beads including the complexes through a density medium, wherein the density medium has a density lower than a density of the beads and higher than a density of the fluid sample, and wherein the transporting occurs, at least in part, by sedimentation; and
   detecting a signal from the labeling agents of the plurality of complexes bound to the plurality of beads.

2. The method of claim 1, wherein said plurality of complexes further comprises a target analyte.

3. The method of claim 2, wherein the target analyte comprises a Staphylococcal enterotoxin B.

4. The method of claim 1, wherein the active toxin is Ricin.

5. The method of claim 1, wherein the active toxin is a Shiga-like toxin.

6. The method of claim 1, wherein the active toxin is a Staphylococcal enterotoxin B.

7. The method of claim 1, wherein the beads comprise silica beads.

8. The method of claim 7, wherein the beads are linked to a DNA or RNA fragment.

9. The method of claim 8, wherein the DNA or RNA fragment is a sarcin-ricin loop.

10. The method of claim 7, wherein the beads are linked to major histocompatibility complex II.

11. The method of claim 1, wherein the labeling agent comprises Apurinic/apyrimidinic (AP) endonuclease (APE1) enzyme.

12. The method of claim 1, wherein the labeling agent comprises a stained immortalized T-cell line.

13. The method of claim 12, wherein the immortalized T-cell line comprises Jurkat cells.

14. The method of claim 13, wherein the Jurkat cells are fixed.

15. The method of claim 14, wherein the Jurkat cells are stained by acridine orange.

16. The method of claim 1, wherein the density medium has a density between about 1.095 g/cc and about 2.05 g/cc.

17. The method of claim 1, wherein said fluid sample comprises whole blood, wherein the density medium has a density greater than a density of red blood cells and the method further comprises:
   separating the red blood cells from the plurality of beads at least in part by applying sedimentation forces to the fluid sample such that the red blood cells remain at an interface between the density medium and fluid sample.

18. A method of conducting a toxin activity assay, the method comprising:
   generating a plurality of complexes on a plurality of beads by action of an active toxin in a fluid sample, individual complexes of the plurality of complexes comprising a sarcin-ricin loop capture agent, and a labeling agent;
   transporting the plurality of beads including the plurality of complexes through a density medium, wherein the density medium has a density lower than a density of the beads and higher than a density of the fluid sample, and wherein the transporting occurs, at least in part, by sedimentation; and
   detecting a signal from the labeling agents of the plurality of complexes bound to the plurality of beads.

19. The apparatus of claim 18, wherein the labeling agent comprises Apurinic/apyrimidinic (AP) endonuclease (APE1) enzyme.

20. The method of claim 19, wherein the active toxin is Ricin.

21. The method of claim 19, wherein the active toxin is a Shiga-line toxin.

22. A method of conducting a toxin activity assay, the method comprising:
   generating a plurality of complexes on a plurality of beads by action of an active toxin in a fluid sample, individual complexes of the plurality of complexes comprising major histocompatibility complex II (MHC) capture agent, and a labeling agent;
   transporting the plurality of beads including the plurality of complexes through a density medium, wherein the density medium has a density lower than a density of the beads and higher than a density of the fluid sample, and wherein the transporting occurs, at least in part, by sedimentation; and
   detecting a signal from the labeling agents of the plurality of complexes bound to the plurality of beads.

23. The method of claim 22, wherein the active toxin is a Staphylococcal enterotoxin B (SEB).

24. The method of claim 23, wherein the labeling agent includes T cell receptors (TCR).

25. The method of claim 24, wherein the TCR include Jurkat cells.

* * * * *